United States Patent [19]

Moran et al.

[11] Patent Number: 5,522,904
[45] Date of Patent: Jun. 4, 1996

[54] COMPOSITE FEMORAL IMPLANT HAVING INCREASED NECK STRENGTH

[75] Inventors: James M. Moran, Hockessin; Richard A. Salzstein, Newark, both of Del.; Isaac M. Daniel, Chicago, Ill.; Douglas S. Cairns, Sandy, Utah; Daniel B. Smith, Warsaw, Ind.

[73] Assignee: Hercules Incorporated, Wilmington, Del.

[21] Appl. No.: 135,484

[22] Filed: Oct. 13, 1993

[51] Int. Cl.⁶ ........................................ A61F 2/32
[52] U.S. Cl. ................. 623/22; 623/23; 623/11; 623/16; 623/18
[58] Field of Search ............... 623/11, 16, 18, 623/22–23, 901

[56] References Cited

U.S. PATENT DOCUMENTS

| | | |
|---|---|---|
| 3,463,158 | 1/1967 | Schmitt et al. |
| 3,893,196 | 7/1975 | Hochman. |
| 4,157,181 | 6/1979 | Cecka. |
| 4,221,623 | 9/1980 | Heissler et al. |
| 4,268,468 | 5/1981 | Esper et al. |

(List continued on next page.)

FOREIGN PATENT DOCUMENTS

| | | |
|---|---|---|
| 0013862 | 1/1979 | European Pat. Off. |
| 0432141A2 | 3/1985 | European Pat. Off. |
| 0177579B1 | 3/1985 | European Pat. Off. |
| 0258406B1 | 2/1987 | European Pat. Off. |
| 0277727 | 1/1988 | European Pat. Off. |
| 2104009 | 4/1972 | France. |
| 2350825 | 12/1977 | France. |
| 2216425 | 10/1989 | United Kingdom. |
| 85/04323 | 10/1985 | WIPO. |
| WO91/18562 | 12/1991 | WIPO. |
| WO92/10353 | 6/1992 | WIPO. |
| WO92/18068 | 10/1992 | WIPO. |
| 93-13733 | 7/1993 | WIPO. |

OTHER PUBLICATIONS

R. Weiss, et al, "High Performance Carbon Fibre Reinforced Polysulfone", *Looking Ahead For Materials and Processes*, pp. 415–428 (Ed. J. de Boussu, et al., Elsevier Science Publishers, Amsterdam, 1987).

F. P. Magee, et al., "A Canine Composite Femoral Stem", *Clinacal Orthopaedics and Related Research*, pp. 237–252 (1988).

E. Morscher, et al., "The Treatment of Femoral Neck Fractures with an Isoelastic Endoprosthesis Implanted Without Bone Cement", *Arch. Orthop. Traumat. Surg.* 98:93–100 (1981).

M. S. Hunt. "Development of Carbon Fibre/Polysulphone Orthopaedic Implants" 1987.

M. S. Hunt. "Fibre Reinforced Composites For Orthopaedic Surgical Implants" 1981.

W. Huettner et al. "Carbon Fiber–Reinforced Polysulphone", Abstr. Program—Bienn. Confr. Carbon 1983, 16th, 482–3; 1983.

W. Hüttner und K. J. Hüttinger. "Verwendung von Kohlenstoff als Implantatmaterial" 81–94; 1983.

K. J. Hüttinger & W. Hüttner. "Carbon Materials for Endoprosthetic Joints". 138–149. 1983.

R. N. King et al. "Novel Uses of Fibers As Tendons and Bones". 335–351. 1977.

(List continued on next page.)

*Primary Examiner*—Randall L. Green
*Assistant Examiner*—P. Zuttarelli
*Attorney, Agent, or Firm*—Mark D. Kuller

[57] ABSTRACT

A femoral implant for a hip prosthesis includes a shaft oriented in a longitudinal direction and a neck extending from said shaft at an acute angle θ to the longitudinal direction. The implant includes a plurality of layers of fibers in a matrix, wherein the fibers are substantially unidirectional in each respective layer. The implant is made from a stack of layers of the matrix so that the direction of fibers is unbalanced. At least 50% of the fibers are oriented in the θ direction and the remainder of said fibers are oriented in directions other than the θ angle.

55 Claims, 3 Drawing Sheets

U.S. PATENT DOCUMENTS

| | | |
|---|---|---|
| 4,329,743 | 5/1982 | Alexander et al. . |
| 4,356,571 | 11/1982 | Esper et al. . |
| 4,397,048 | 8/1983 | Brown et al. . |
| 4,403,606 | 9/1983 | Woo et al. . |
| 4,411,027 | 10/1983 | Alexander et al. . |
| 4,459,708 | 7/1984 | Buttazzoni . |
| 4,506,681 | 3/1985 | Mundell . |
| 4,512,038 | 4/1985 | Alexander et al. . |
| 4,662,887 | 5/1987 | Turner et al. . |
| 4,714,467 | 12/1987 | Lechner et al. . |
| 4,738,681 | 4/1988 | Koeneman et al. . |
| 4,750,905 | 6/1988 | Koeneman et al. . |
| 4,778,469 | 10/1988 | Lin et al. . |
| 4,892,552 | 1/1990 | Ainsworth et al. . |
| 4,902,297 | 2/1990 | Devanathan . |
| 4,978,360 | 12/1990 | Devanathan . |
| 5,064,439 | 11/1991 | Chang et al. . |
| 5,163,962 | 11/1992 | Salzstein et al. . |
| 5,181,930 | 1/1993 | Dumbleton et al. . |

OTHER PUBLICATIONS

Moshe Roffman, M. D. et al. "Carbon Fiber Reinforced Polysulfone Hip Implant: Experimental Study in Dogs". Oct. 1 Oct. 3. 1985.

Derwent Abstract of French Patent No. 2.104.009.

Derwent Abstract of US 3,893,196.

Derwent Abstract of French Patent No. 2.350.825 and DE 2625529.

Derwent Abstract of DE 2621123.

Derwent Abstract of DE 2621124.

D. Scola et al, "The Effect of Process Variables on the Dry and Wet Shear Strength of Fiber Reinforced Polysulfone Composites", Proc. 23rd Nat. Synp. Exhib. Adv. Mat. Process Eng. (1978).

Huttinger et al., "Carbon Materials for Endoprosthetic Joints", Extended Abstracts of the International Symposium on Carbon, 1982, pp. 138–149.

Gillespie, Jr. et al., "CMAP—Composite Materials Analysis of Plates", CCM Report 87–45, Center for Composite Materials, University of Delaware, 1987.

Bergmann et al., "Hip Joint Loading During Walking and Running, Measured in Two Patients," submitted for publication to Journal of Biomechanics, 1992.

International Organization for Standardization, "Implants for Surgery–Partial and Total Hip Joint Prostheses: Part 6: Determination of Endurance Properties of Head and Neck Region of Stemmed Femoral Components", ISO 7206–6, 1992.

Gregory Born McKenna, "The Development of Fiber Reinforced Polymer Composites for Orthopedic Applications", Xerox University Microfilms, Ann Arbor, Michigan, 1976, pp. 226–232.

Kenneth R. St. John, "Applications of Advanced Composites In Orthopaedic Implants", Biocompatible Polymers, Metals, And Composites, Technomic Publishing Co., Inc., Lancaster, PA., 1983, pp. 861–871.

L. Claes et al., "Experimental Investigations On Hip Prostheses With Carbon Fibre Reinforced Carbon Shafts and Ceramic Heads" Ceramics In Surgery, Elsevier Scientific Publishing Company,Amsterdam, The Netherlands, 1983, pp. 243–250.

M. S. Hunt, "Carbon Fibre Reinforced Polysulphone for Orthopaedic Surgical Implants", International Conference Biomedical Polymers—International Symposium—Contact lenses & Artificial Eyes, The Biological Engineering Society, London, 1982, pp.89–96.

L. Srinivasa Iyer et al., "Development of Optimized Epoxy Graphite Implant for the Total Hip Joint", ISA Transactions, vol. 23, No. 2, 1984, pp. 7–14.

"The Effect of Process Variables on the Dry And Wet Shear Strength of Fiber Reinforced Polysulfone Composites", by Daniel A. Scola and Margaret E. Roylance.

COMPOSITE FEMORAL IMPLANT HAVING INCREASED NECK STRENGTH

BACKGROUND OF THE INVENTION

1. Field of the Invention

The present invention relates to a femoral implant used as a hip-joint prosthesis. In particular, the invention relates to implants made of composite laminates of continuous fiber in a matrix. For example, the fibers may be carbon, boron, ceramic, metal, aramid fibers (e.g. Kevlar), or fiberglass, and the matrix may be biocompatible a polymer, metal, ceramic, or carbon.

2. Discussion of Background Information

A femoral implant, as the name implies, replaces the end of a femur in a hip-joint prosthetic device. The femoral implant basically includes a longitudinal stem or shaft that is connected to bone. In present practice, the stem sits in a cavity formed in the proximal region of the femur. A neck extends from the shaft terminating in a ball, which cooperates with the acetabulum, or socket, of the hip joint in the pelvis. To insert the implant, the head of the femur is removed and a cavity formed in the bone just below the cut. The shaft of the implant is then anchored into the cavity using, e.g., a press-fit or bone cement.

Implants made of fiber embedded in a polymeric matrix have been used in place of earlier metal implant designs. Fiber-matrix composite implants can be engineered to exhibit structural properties more closely resembling that of natural bone, which has less of an adverse effect than implants much stiffer than natural bone.

One method of making an implant of continuous unidirectional fiber involved stacking layers having parallel conditions unidirectional fibers in a matrix, in which the orientation of the fiber in each layer was arranged in a parallel manner. The orientation of the fiber in the final implant could then be varied by stacking the individual layers in such a way that the fibers were aligned in the desired direction. The final product was produced by heating the matrix in which the fibers were embedded in order to cause the matrix to flow. Upon cooling, the matrix hardened into a composite block in which the various layers of fiber were aligned as desired.

Fibers were aligned in these composite blocks in directions wherein increased strength was considered to provide optimum results. For example, reinforcement was provided along the shaft, i.e., the longitudinal axis, by orienting a majority of the fibers in that direction. Reinforcement was also provided by orienting fibers at an acute angle to the longitudinal direction, balanced by fibers oriented in the negative acute angle direction, producing a mirror image about a sagittal plane of the device. However, it was believed that the shaft region should be more strongly reinforced than the neck region. For example, see U.S. Pat. No. 4,892,552 and "Carbon Materials For Endoprosthetic Joints", K.J. Hüttinger and W. Huettner, Extended Abstracts of the International Symposium on Carbon, 1982, pages 138–149, the disclosures of which are incorporated by reference in their entireties.

Also, U.S. Pat. No. 5,064,439, the disclosure of which is hereby incorporated by reference in its entirety, discloses a load-bearing prosthetic device, such as a hip stem with a longitudinally curved body. The prosthetic device is made from continuous filament fiber plies with parallel oriented fibers in each ply. The plies are curved longitudinally to correspond to the shape of the body. In one embodiment, the plies at or near the surfaces have longitudinally oriented fibers and the plies between the surface layers have fibers offset at 5°–40° from the longitudinal axis. The fiber orientation is balanced by providing a ply of negatively angled offset fibers for each positively angled offset ply. Table III of U.S. Pat. No. 5,064,439 shows examples of unbalanced fiber orientations. None of the examples, however, teach a fiber orientation wherein at least 50% of the layers have fibers oriented in the $\theta$ direction and the remainder of the layers have fibers oriented in directions other than the $\theta$ angle, where $\theta$ is the acute angle formed between the longitudinal direction of the shaft and the neck extending therefrom.

A femoral implant made from layers of fiber in a polymeric matrix is disclosed in U.S. Pat. No. 5,163,962, the disclosure of which is hereby incorporated by reference in its entirety. The femoral implant has a longitudinal shaft having a neck extending therefrom at an acute angle $\theta$ to the longitudinal direction. The layers of fibers are arranged such that they are balanced with at least 50% of the layers in the $\pm\theta$ directions.

SUMMARY OF THE INVENTION

The invention is a femoral implant for a hip prosthesis comprising a shaft oriented in a longitudinal direction; a neck extending from said shaft at an acute angle $\theta$ to the longitudinal direction. The implant comprises a plurality of layers of fibers in a matrix, wherein said fibers are substantially unidirectional in each respective layer. At least 50% of said fibers are oriented in the $\theta$ direction and the remainder of said fibers are oriented in directions other than the $\theta$ angle.

According to another embodiment, the invention is a femoral implant for a hip prosthesis comprising: a shaft oriented in a longitudinal direction; a neck extending from said shaft at an acute angle $\theta$ to the longitudinal direction; said implant comprises a plurality of layers of fibers in a matrix, wherein said fibers are substantially unidirectional in each respective layer; wherein more of said fibers are oriented in the $\theta$ direction than are fibers oriented in directions other than the angle.

According to yet another embodiment, the invention is a femoral implant for a hip prosthesis comprising a shaft; oriented in a longitudinal direction and a neck extending from said shaft at an acute angle $\theta$ to the longitudinal direction. The implant comprises a plurality of layers of fibers in a mat, wherein said fibers are substantially unidirectional in each respective layer. At least as many of said fibers are oriented in the $\theta$ direction as are fibers oriented in the shaft direction, the number of fibers oriented in the $\theta$ direction being different than the number of fibers oriented in the shaft direction.

The invention is also directed to a method of making a femoral implant for hip prosthesis having a shaft oriented in a longitudinal direction and a neck extending from said shaft at an acute angle $\theta$ to said longitudinal direction. The method comprises the steps of forming a plurality of individual layers of substantially unidirectional fibers in a matrix; stacking said layers such that at least 50% of said fibers are oriented at said angle $\theta$ and the remainder are oriented in directions other than the $\theta$ angle; heating the stacked layers under pressure to melt said matrix; cooling said matrix to form a composite block; and machining said stacked layers into the form of the implant.

The invention is further directed to a method of performing lip-joint replacement surgery comprising implanting a femoral implant. The implant comprises a shaft oriented in a longitudinal direction and a neck extending from said shaft at an acute angle θ to the longitudinal direction. The implant comprises a plurality of layers of fibers in a matrix wherein said fibers are unidirectional in each respective layer. At least 50% of said layers have fibers oriented in the θ direction and the remainder of said layers have fibers oriented in directions other than the θ angle.

The present invention is also directed to a femoral implant for a hip prosthesis including a shaft oriented in a longitudinal direction and a neck extending from said shaft at an acute angle θ to the longitudinal direction. The implant may be made from layers of fiber in a matrix wherein the fibers are unidirectional in each layer. The implant is made from a stack of layers of fibers and matrix so that the direction of the fibers is unbalanced. At least 50% of the layers have fibers oriented in the θ direction and the remainder of the layers have fibers oriented in directions other than the θ angle. For example, the remainder of the fibers can be oriented within ±10° from the longitudinal direction. Also, more of the fibers may be oriented in the θ direction than are fibers oriented in directions other than the θ angle, or at least as much of the fibers are oriented in the θ direction as are fibers oriented in the shaft direction, the number of fibers oriented in the θ direction being different than the number of fibers oriented in the shaft direction. The claimed invention is useful in humans, mammals and other animals.

A further embodiment of the invention provides a method of making a femoral implant for a hip prosthesis having a shaft oriented in a longitudinal direction and a neck extending from the shaft at an acute angle θ to the longitudinal direction. The method includes forming individual layers of substantially unidirectional fibers in a matrix, stacking the layers such that at least 50% of the layers have fibers oriented in the θ direction and the remainder of the layers have fibers oriented in directions other than the θ angle; heating the stacked layers under pressure to consolidate the matrix; cooling the matrix to form a composite block; and machining the block into the form of the implant. Alternatively, the stacked layers may be machined into the form of the implant and then heated to consolidate the matrix.

A still further embodiment of the invention provides a method of performing hip-joint replacement surgery comprising implanting a femoral implant including a shaft oriented in a longitudinal direction and a neck extending from the shaft at an acute angle θ to the longitudinal direction. The implant is made from layers of fiber in a matrix wherein the fibers are unidirectional in each layer. At least 50% of the layers have fibers oriented in the θ direction and the remainder of the layers have fibers oriented in directions other than the θ angle.

In accordance with the present invention, it was discovered that a femoral implant composite device does not require primary reinforcement in the shaft because that part of the device is firmly supported by the femur. In fact, flexibility in the stem is important in order to permit stress transmission to the bone to forestall bone resorption. On the other hand, the neck of the device protrudes above, and at an angle to, the femur. Since the neck is not surrounded by bone, it will not benefit from bone support, and flexibility in the neck is not as important as it is in the stem.

Accordingly, it has been discovered that the claimed invention, an implant made from layers of fibers wherein the direction of the fibers is unbalanced, provides a composite design that maximizes strength in the neck region while maintaining sufficient flexibility and strength in the shaft region.

DETAILED DESCRIPTION OF THE PREFERRED EMBODIMENTS

Various types of fiber are useful in accordance with the presently claimed invention. For example, the fiber may be made from carbon. Such fibers are well known and commonly used in the manufacture of fiber composite hip prostheses as disclosed in U.S. Pat. No. 4,512,038, the disclosure of which is hereby incorporated by reference in its entirety. The manufacture of composite materials containing layers of fiber embedded in a matrix and prosthetic devices from blocks of composite material containing fiber at differing angles of orientation is well known as disclosed in U.S. Pat. No. 4,892,552 and Proc. 234d Nat. Symp. Exhib. Adv. Mat. Process Eng., p. 250 (1978), the disclosures of which are hereby incorporated by reference in their entireties. For example, a continuous carbon fiber tow is drawn through a solvent solution of a polymeric matrix. The coated fiber is then wound on a drum to form a layer. Upon drying, the material on the drum is slit along the length of the drum and a coherent layer of material is unwound into a sheet. Rectangular pieces are then cut from the sheet in such a way that the fibers are oriented in the rectangle at the desired angle. A stack of the rectangles is prepared containing the desired fiber orientation, which is then heated under pressure to form a single block of the composite material.

In arranging the composite layers in accordance with the present invention, it is preferable that the completed stack have at least 50% of the layers with fibers oriented in the θ direction and the remainder oriented in the longitudinal direction or at angles other than the θ angle; that is, the remainder of the fibers may be oriented in directions other than the shaft and θ directions. Preferably, each block contains about 100–300 layers.

Figure 1:
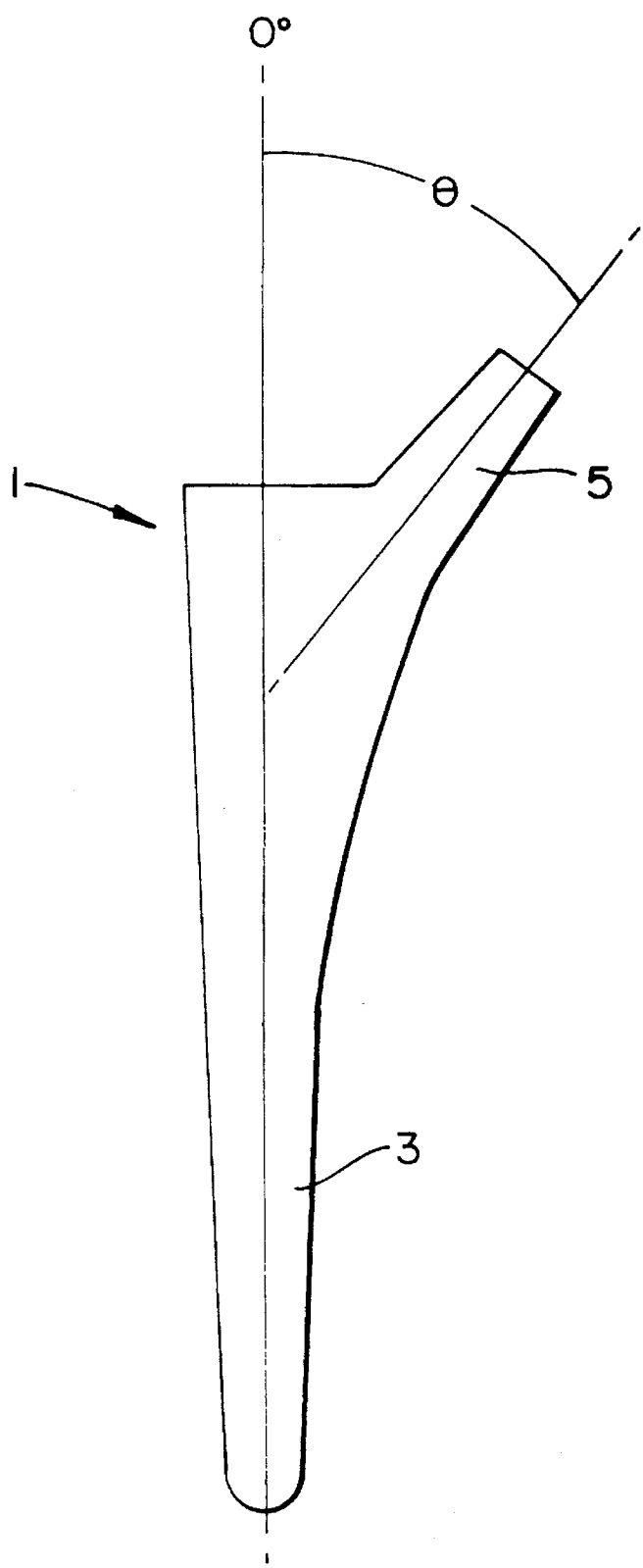
FIG. 1 is a schematic view showing the orientation of a preferred embodiment of the present invention.

With reference to FIG. 1, a preferred embodiment of the presently claimed invention is machined from a composite block of material so that implant 1 has a shaft 3 disposed in the 0° or longitudinal direction. Neck 5 projects at angle θ to the longitudinal direction from shaft 3. Preferably, angle θ is about 25°–55°, and may include tolerances of ±5°. Angle θ may be in the following ranges: 30°–55°, 35°–55°, 40°–55°, 45°–55°, 25°–50°, 25°–45°, and 35°–45°. Preferably, angle θ is about 40°. Accordingly, at least 50% of the layers have fibers oriented in the θ direction and the remainder are oriented in directions other than the θ angle. Preferably about 50 to 60% of the layers have fibers oriented in the θ direction and about 40 to 50% of the remainder are oriented in the longitudinal direction. It is noted that each layer may have a different number of fibers. Alternately, the remaining plies may be oriented at two or more angles between the θ and longitudinal directions. This may modulate the stem stiffness and the neck and stem strength. Also, the fibers are preferably substantially continuous. Composites made of long discontinuous fibers, greater than ⅛ inch in length have been developed. These fibers may be oriented in individual plies and may be useful in the present invention.

Figure 2:
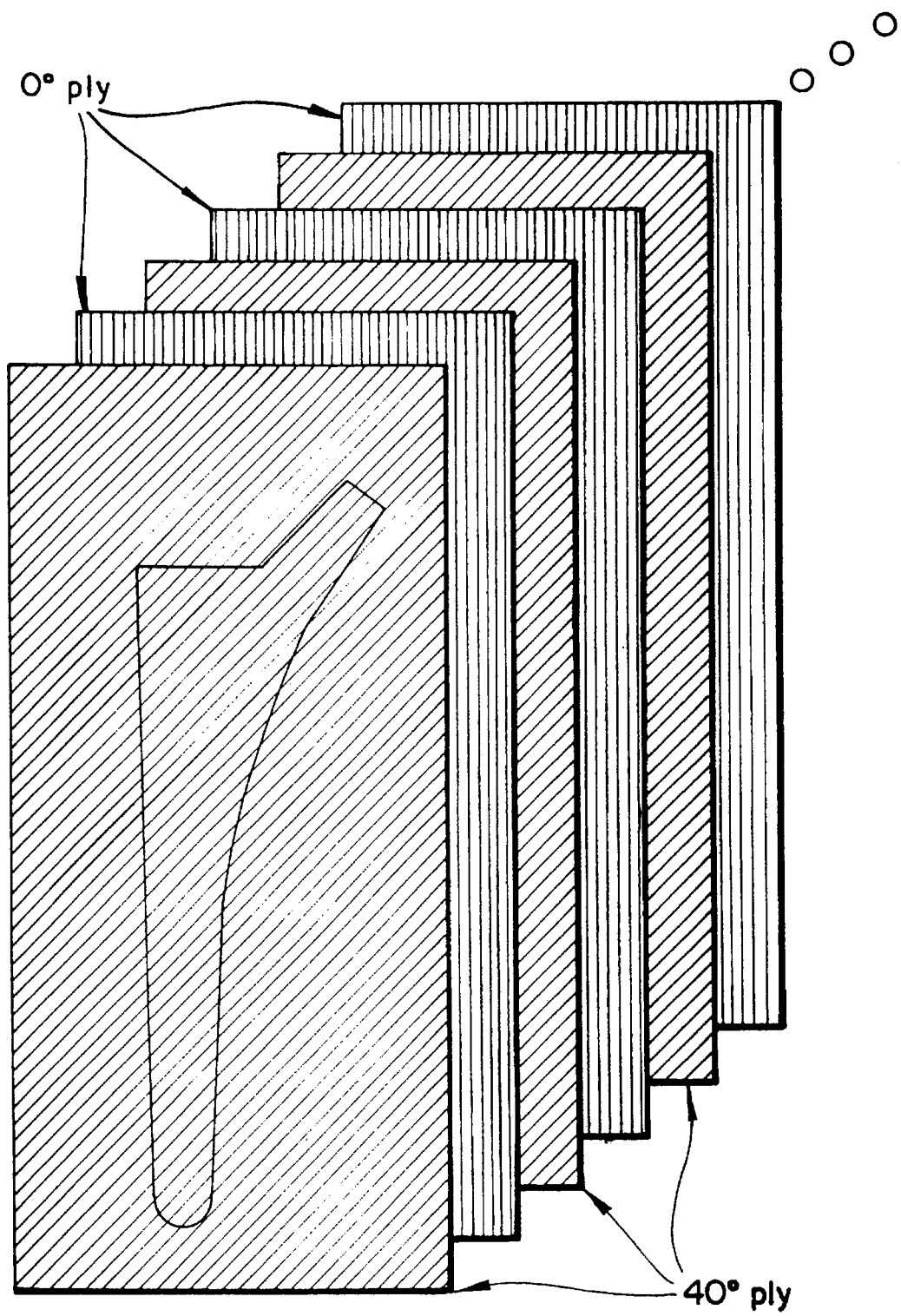
FIG. 2 is an exploded perspective view of a stage in the production of a preferred embodiment of the present invention.

For example, with reference to FIG. 2, an arrangement of layers is shown with 50% of the layers having fibers oriented in the angle of the neck and the remainder oriented in the longitudinal direction. The outline of the femoral implant appears on the foremost layer. The stack is then placed in a mold and heated under pressure in order to form a composite block of the matrix in which the individual layers of fiber are contained. The composite block is then machined according to well known procedures in order to fashion the desired femoral implant, such as disclosed in the aforesaid U.S. Pat. No. 4,512,038. Alternatively, the composite block may be machined into the form of the implant and then heated to consolidate the matrix.

The amount of matrix in the implant is sufficient to provide cohesiveness among the carbon fibers. Preferably matrix content varies from 20–80% by volume, more preferably 38–44%, of the implant, with carbon fiber making up the remainder. Useful materials for the matrix are ceramic, metal, carbon, or polymer. Polymers may be thermosets, such as epoxies or acrylics, or engineering thermoplastics as disclosed in the aforesaid U.S. Pat. No. 4,892,552, such as polysulfone, polyethersulphone, polyarylsulfone, polyphenylene sulfide, polycarbonates, aromatic polyamides, aromatic polyamideimides; thermoplastic polyimides, polyaryletherketones, polyetheretherketones, polyarylethernitriles, aromatic polyhydroxyethers, and the like. Preferably, the matrix is biocompatible and a medical grade polysulfone resin.

The size of the individual layers used to make the composite block varies depending on the size of fiber used, the amount of fiber in the individual layer, and how much material coats the fiber. Preferably, the layers are 0.1–0.5 mm thick, more preferably 0.15–0.35 mm. Sufficient layers are used to form a composite block having dimensions large enough for the femoral implant. Preferably, the block is about 20–50 mm thick.

Figure 3:
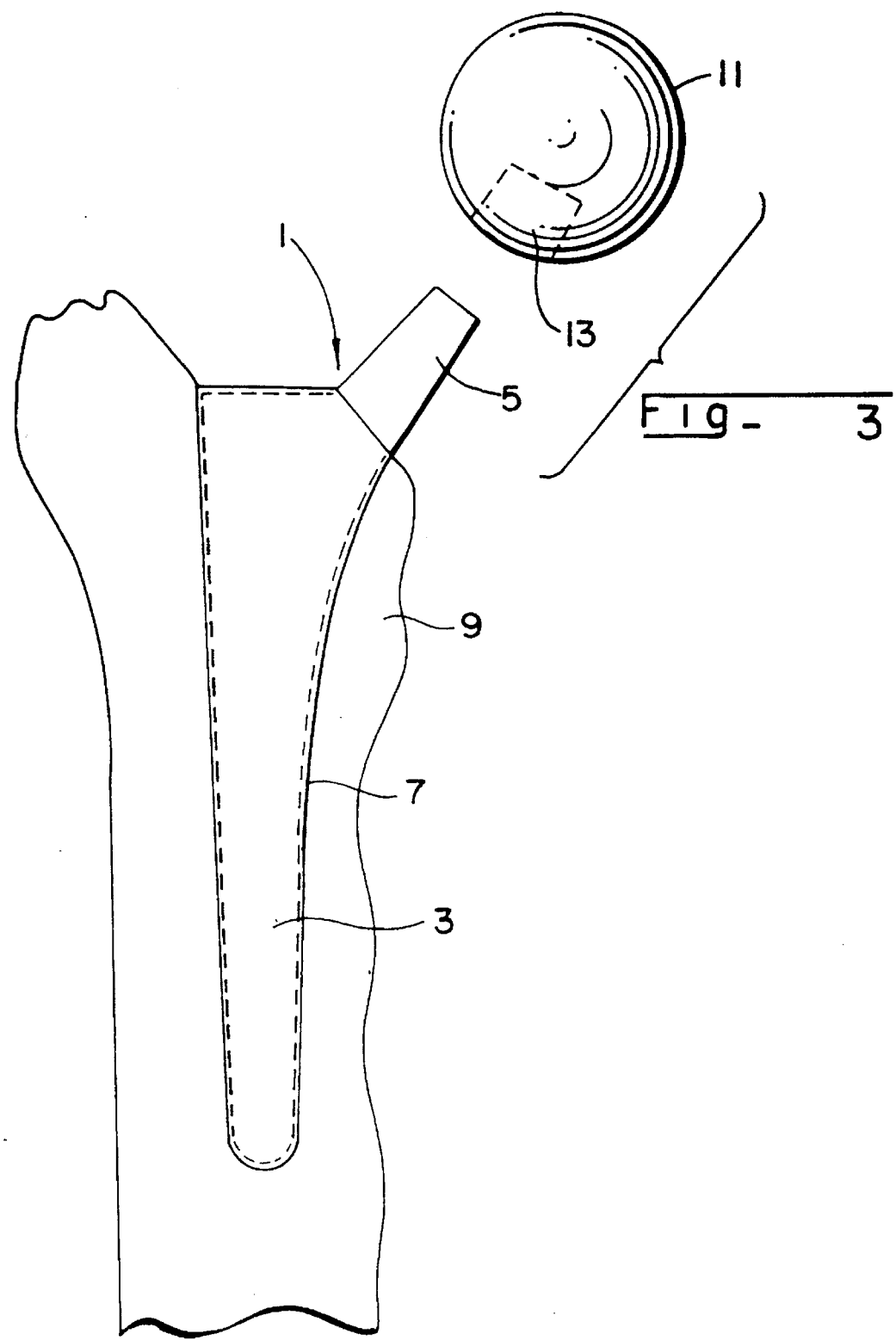
FIG. 3 is a schematic view showing the use of a preferred embodiment of the present invention.

With reference to FIG. 3, use of a preferred embodiment of the present invention is described. Shaft 3 of implant 1 is anchored in cavity 7 of femur 9. Neck 5 of implant 1 is fixed to ball 11, which is designed to cooperate with the acetabulum of the pelvis (not shown). The ball is made of known surgical alloys comprised, e.g., of titanium-aluminum-vanadium or cobalt-chromium-molybdenum, or of a ceramic material, according to known methods. A cobalt 13 in ball 11 and the neck 5 of the implant are machined tapered (i.e., Morse taper) to mate as is well known in the art. During surgery a ball is correctly selected by the surgeon for size and press-fit onto the neck. Surgical procedures for attaching femoral implants are well known.

Preferably, the femoral implant of the present invention further contains an encapsulating layer of the matrix. This is accomplished, e.g., by vacuum thermoforming two sheets of neat polymer for placement around the composite. Vacuum thermoforming is a well known technique that will be readily applicable by the skilled artisan. Typically, this is accomplished by heating two sheets of the polymer to a sufficient temperature to make the sheets moldable. Vacuum is then used to draw the sheets: into a cavity having he dimensions of either the front or back surface of the composite implant core plus the film thickness. When cooled, the sheets are trimmed to create preforms. A pair of preforms is then placed on either side of the composite and compressed between a mold to encapsulate the composite, each preform comprising, in effect, one-half of the encapsulating layer. Advantageously, the mold conveys a textured relief to each side of the encapsulating layer, which aids in anchoring the implant in the femur. Optionally, a physiologically acceptable radiopaque material, such as barium sulfate at about 2–10% by weight of the sheet, is contained in the encapsulating sheets. This enables positioning of the device to be more readily determined radiographically. Alternatively, radio-dense markers may be inserted into the device for this purpose.

The benefit of the present invention can be shown by computer modeling of the compressive strength of the composite material. Computer modeling based on laminate plate theory is disclosed by "CMAP—Composite Material Analysis of Plates", CCM Report 87-45, J.W. Gillespie, Jr., L.J. Shuda, B. Walbel, J.J. Garrett, and J. Snowden, Center For Composite Materials, University of Delaware, 1987, the disclosure of which is hereby incorporated by reference in its entirety. Three polysulfone/carbon fiber laminates were compared: [0°,+40°], [0°, +40°, 0°, −40°], and [0°, +40°, 0°, −40°, 0°] where 40° is the neck angle. The first laminate [0°, 40°] is within the scope of the present invention. The results of the analysis are shown in the following table:

| PLY ORIENTATION | COMPRESSIVE STRENGTH (NECK DIRECTION, KSI) |
| --- | --- |
| [0°, 40°] | 80 |
| [0°, +40°, 0°, −40°] | 52 |
| [0°, +40°, 0°, −40°, 0°] | 45 |

In order to more clearly describe the present invention, the following non-limiting example is provided.

EXAMPLE

Carbon fiber tow containing about 12,000 fibers, each about 7 μm in diameter (available from Hercules Incorporated under the designation AS4) is drawn over rollers submerged in a solution of polysulfone resin. (UDEL MG11 available from Amoco Performance Products) in methylene chloride to coat the fibers with resin. The resin-impregnated tow is taken up on a revolving polytetrafluoroethylene-coated drum (10.0–12.5" in diameter and 3' long) to form a continuous cylindrical sheet in which adjacent tow strands, 0.5" wide, overlap each other about 0.25". The sheet is removed from the drum when the solvent has evaporated by slitting the dried material on the drum along the drum axis to form a flat rectangular sheet about 0.25 mm thick. Rectangular coupons are cut from the sheet so as to obtain coupons having fibers oriented with respect to the length of the rectangle at 0° and +40°.

A stack of the coupons is formed such that the length of the rectangle represents the axis of the shaft of the femoral implant, i.e., the 0° direction. Starting from the bottom of the block, the first coupon contains fibers oriented +0° relative to the longitudinal axis and is followed by a layer containing fibers oriented +40°. The foregoing stacking sequence is represented according to code as follows: [0°,+40°]n. The sequence, [0°,+40°], is repeated "n" times to create the block. The total number of coupons in the stack varies from 100–300, depending on the desired size of the implant.

The stack of coupons is placed in a 10"×10" mold and compression molded at about 100 psi and 293° C. to form a block of the composite material. The longitudinal modulus of the composite is about 8 msi. A core femoral implant is machined from the block using well known techniques to a shape approximating that in FIG. 1. Supporting the neck of the device, at least 50% of the lamina are the +40° plies. The core is then encapsulated in the same polysulfone resin used to impregnate the fibers by vacuum-thermoforming matched pairs of preforms and compression molding them to the core at 195°–200° C. for about 11 minutes.

Although the invention has been described with reference to particular materials and embodiments, it is to be understood that the invention is not limited to the particulars disclosed and extends to all equivalents within the scope of the claims.

What is claimed:

1. A femoral implant for a hip prosthesis comprising:

a shaft oriented in a longitudinal direction; a neck extending from said shaft at an acute angle θ to the longitudinal direction; said implant comprises a plurality of layers of fibers in a matrix, wherein said fibers are substantially unidirectional in each respective layer; wherein at least 50% of said fibers of the implant are oriented in the θ direction and the remainder of said fibers of the implant are oriented in directions other than the θ angle.

2. The implant according to claim 1, wherein about 50 to about 60% of said fibers are oriented in the θ direction.

3. The implant according to claim 1, wherein about 40 to about 50% of said fibers are oriented in the longitudinal direction.

4. The implant according to claim 1, wherein said acute angle θ is about 25°–55°.

5. The implant according to claim 1, wherein said matrix comprises a biocompatible matrix.

6. The implant according to claim 1, wherein said matrix comprises a polymeric matrix.

7. The implant according to claim 1, wherein said matrix is selected from the group consisting of polysulfone, polyethersulphone, polyarylsulfone, polyphenylene sulfide, polycarbonates, aromatic polyamides, aromatic polyamideimides, thermoplastic polyimides, polyaryletherketones, polyetheretherketones, polyarylethernitriles, aromatic polyhydroxyethers, and mixtures thereof.

8. The implant according to claim 1, wherein said matrix is selected from the group consisting of ceramics, metals, carbon, epoxies, acrylics, and mixtures thereof.

9. The implant according to claim 1, wherein said matrix comprises polysulfone resin.

10. The implant according to claim 1, wherein said fibers comprise carbon.

11. The implant according to claim 1, wherein said fibers comprise a ceramic material.

12. The implant according to claim 1, wherein said fibers comprise boron.

13. The implant according to claim 1, wherein said fibers comprise metal.

14. The implant according to claim 1, wherein said fibers comprise a polymer.

15. The implant according to claim 1, wherein said fibers comprise aramid fibers.

16. The implant according to claim 1, wherein said fibers comprise fiberglass.

17. The implant according to claim 1, wherein said remainder of said fibers are oriented in the longitudinal direction.

18. The implant according to claim 1, wherein the number of layers is at least 100.

19. The implant according to claim 1, wherein the number of layers is about 100–300.

20. The implant according to claim 1, wherein the compressive strength of the neck is at least about 80 ksi.

21. The implant according to claim 1, wherein said acute angle θ is about 25°–55°, said layers are flat, said matrix comprises a biocompatible matrix, and said fibers are selected from the group consisting of carbon, ceramic, boron, metal, aramid and fiberglass fibers.

22. The implant according to claim 1, wherein said acute angle θ is about 35°–45°, said layers are flat, said matrix comprises a biocompatible polymeric matrix, said fibers comprise carbon and the number of layers is about 100–300.

23. A femoral implant as in claim 1 wherein the remainder of the fibers are oriented within ±10° from the longitudinal direction.

24. The implant according to claim 1, wherein said acute angle θ is about 35°–45°.

25. The implant according to claim 24, wherein said acute angle θ is about 40°.

26. A femoral implant for a hip prosthesis comprising:

a shaft oriented in a longitudinal-direction and a neck extending from said shaft at an acute angle θ to the longitudinal direction; wherein said implant comprises a plurality of layers of fibers in a matrix, wherein said fibers are substantially unidirectional in each respective layer; and wherein more of said fibers of the implant are oriented in the θ direction than are fibers of the implant oriented in directions other than the θ angle.

27. The implant according to claim 26, wherein more of said fibers are oriented in the θ direction than in the longitudinal direction.

28. The implant according to claim 26, wherein said acute angle θ is about 25°–55°, said layers are flat, said matrix comprises a biocompatible matrix, and said fibers are selected from the group consisting of carbon, ceramic, boron, metal, aramid and fiberglass fibers.

29. The implant according to claim 26, wherein said acute angle θ is about 35°–45°, said layers are flat, said matrix comprises a biocompatible polymeric matrix, said fibers comprise carbon and the number of layers is about 100–300.

30. A femoral implant for a hip prosthesis comprising: a shaft oriented in a longitudinal direction and a neck extending from said shaft at an acute angle θ to the longitudinal direction; wherein said implant comprises a plurality of layers of fibers in a matrix, wherein said fibers are substantially unidirectional in each respective layer; and wherein more of said layers contain fibers oriented in the θ direction than said layers contain fibers oriented in the shaft direction.

31. The implant according to claim 30, wherein said acute angle θ is about 25°–55°, said layers are flat, said matrix comprises a biocompatible matrix, and said fibers are selected from the group consisting of carbon, ceramic, boron, metal, aramid and fiberglass fibers.

32. The implant according to claim 30, wherein said acute angle θ is about 35°–45°, said layers are flat, said matrix comprises a biocompatible polymeric matrix, said fibers comprise carbon and the number of layers is about 100–300.

33. A method of making a femoral implant for a hip prosthesis having a shaft oriented in a longitudinal direction and a neck extending from said shaft at an acute angle θ to said longitudinal direction comprising the steps of: forming a plurality of individual layers of substantially unidirectional fibers in a matrix; stacking said layers such that at least 50% of said fibers of the implant are oriented at said angle θ and the remainder are oriented in directions other than the θ angle; heating the stacked layers under pressure to melt said matrix; cooling said matrix to form a composite block; and machining said stacked layers into the form of the implant.

34. The method according to claim 33, wherein said acute angle θ is about 25°–55°, said layers are flat, said matrix comprises a biocompatible matrix, and said fibers are selected from the group consisting of carbon, ceramic, boron, metal, aramid and fiberglass fibers.

35. The method according to claim 33, wherein said acute angle θ is about 35°–45°, said layers are flat, said matrix comprises a biocompatible polymeric matrix, said fibers comprise carbon and the number of layers is about 100–300.

36. A method of performing hip-joint replacement surgery comprising implanting a femoral implant comprising a shaft oriented in a longitudinal direction and a neck extending from said shaft at an acute angle θ to the longitudinal direction; wherein said implant comprises a plurality of layers of fibers in a matrix wherein said fibers are unidirectional in each respective layer; and wherein at least 50% of said layers have fibers oriented in the θ direction and the remainder of said layers have fibers oriented in directions other than the θ angle.

37. The method according to claim 36, wherein said acute angle θ is about 25°–55°, said layers are flat, said matrix comprises a biocompatible matrix, and said fibers are selected from the group consisting of carbon, ceramic, boron, metal, aramid and fiberglass fibers.

38. The method according to claim 36, wherein said acute angle θ is about 35°–45°, said layers are flat, said matrix comprises a biocompatible polymeric matrix, said fibers comprise carbon and the number of layers is about 100–300.

39. A femoral implant for a hip prosthesis comprising a shaft oriented in a longitudinal direction and a neck extending from said shaft at an acute angle θ to the longitudinal direction; wherein said implant comprises a plurality of layers of fibers in a matrix, and said fibers are substantially unidirectional in each respective layer; and wherein at least 50% of the layers have fibers oriented in the θ direction and the remainder of the layers have fibers oriented in directions other than the θ angle.

40. A femoral implant for a hip prosthesis as claimed in claim 39 wherein the implant is made from a stack of layers of fibers and matrix so that the direction of the fibers is unbalanced.

41. A femoral implant as in claim 39 wherein more of the fibers may he oriented in the θ direction than are fibers oriented in directions other that the θ angle.

42. A femoral implant as in claim 39 wherein at least as much of the fibers are oriented in the θ direction as are fibers oriented in the shaft direction, the number of fibers oriented in the θ direction being different than the number of fibers oriented in the shaft direction.

43. A femoral implant according to claim 39, wherein said acute angle θ is about 25°–55°, said layers are flat, said matrix comprises a biocompatible matrix, and said fibers are selected from the group consisting of carbon, ceramic, boron, metal, aramid and fiberglass fibers.

44. A femoral implant according to claim 39, wherein said acute angle θ is about 35°–45°, said layers are flat, said matrix comprises a biocompatible polymeric matrix, said fibers comprise carbon and the number of layers is about 100–300.

45. A femoral implant as in claim 39 wherein the remainder of the fibers are oriented within ±10° from the longitudinal direction.

46. A femoral implant according to claim 45, wherein said acute angle θ is about 25°–55°, said layers are flat, said matrix comprises a biocompatible matrix, and said fibers are selected from the group consisting of carbon, ceramic, boron, metal, aramid and fiberglass fibers.

47. A femoral implant according to claim 45, wherein said acute angle θ is about 35°–45°, said layers are flat, said matrix comprises a biocompatible polymeric matrix, said fibers comprise carbon and the number of layers is about 100–300.

48. A method of making a femoral implant for hip prosthesis having a shaft oriented in a longitudinal direction and a neck extending from said shaft at an acute angle θ to said longitudinal direction comprising the steps of: forming a plurality of individual layers of substantially unidirectional fibers in a matrix; stacking the layers such that at least 50% of the layers have fibers oriented in the θ direction and the remainder of the layers have fibers oriented in directions other than the θ angle; heating the stacked layers under pressure to melt said matrix; cooling said matrix to form a composite block; and machining said stacked layers into the form of the implant.

49. A method of making a femoral implant for hip prosthesis as claimed in claim 48 wherein said heating step is carried out prior to said maching step.

50. A method of making a femoral implant for hip prosthesis as claimed in claim 48 comprising sequentially said machining the stacked layers into the form of the implant and then said heating the stacked layers under pressure to melt said matrix.

51. The method according to claim 48, wherein said layers are flat, said acute angle θ is about 25°–55°, said matrix comprises a biocompatible matrix, and said fibers are selected from the group consisting of carbon, ceramic, boron, metal, aramid and fiberglass fibers.

52. The method according to claim 48, wherein said acute angle θ is about 35°–45°, said layers are flat, said matrix comprises a biocompatible polymeric matrix, said fibers comprise carbon and the number of layers is about 100–300.

53. The method according to claim 48, wherein said acute angle θ is about 25°–55°, said layers are flat, said matrix comprises a biocompatible matrix, and said fibers are selected from the group consisting of carbon, ceramic, boron, metal, aramid and fiberglass fibers.

54. The method according to claim 48, wherein said acute angle θ is about 35°–45°, said layers are flat, said matrix comprises a biocompatible polymeric matrix, said fibers comprise carbon and the number of layers is about 100–300.

55. A method of performing hip-joint replacement surgery comprising implanting a femoral implant comprising a shaft oriented in a longitudinal direction and a neck extending from said shaft at an acute angle θ to the longitudinal direction; wherein said implant comprises a plurality of layers of fibers in a matrix and said fibers are unidirectional in each respective layer; and wherein at least 50% of said layers have fibers oriented in the θ direction and the remainder of said layers have fibers oriented in directions other than the θ angle.

* * * * *